United States Patent [19]

Rozov et al.

[11] Patent Number: 5,283,372
[45] Date of Patent: Feb. 1, 1994

[54] PREPARATION OF PURIFIED OPTICAL ISOMERS OF DESFLURANE

[75] Inventors: Leonid A. Rozov, Fair Lawn; Chialang Huang, Edison; Donald F. Halpern, Fanwood; Gerald G. Vernice, Nutley, all of N.J.

[73] Assignee: Anaquest, Inc., Liberty Corner, N.J.

[21] Appl. No.: 48,091

[22] Filed: Apr. 15, 1993

Related U.S. Application Data

[60] Division of Ser. No. 959,204, Oct. 9, 1992, abandoned, which is a continuation of Ser. No. 802,115, Dec. 4, 1991, abandoned.

[51] Int. Cl.$^5$ .............................................. C07C 41/22
[52] U.S. Cl. .................................................... 568/683
[58] Field of Search ......................................... 568/693

[56] References Cited

U.S. PATENT DOCUMENTS

| | | | |
|---|---|---|---|
| 4,762,856 | 8/1988 | Terrell | 514/722 |
| 5,015,781 | 5/1991 | Robin et al. | 568/683 |
| 5,114,714 | 5/1992 | Young et al. | 424/400 |
| 5,114,715 | 5/1992 | Young et al. | 424/400 |

Primary Examiner—Howard T. Mars
Attorney, Agent, or Firm—R. Hain Swope; Larry R. Cassett

[57] ABSTRACT

A process for the preparation of highly purified optical isomers of desflurane, i.e. 2-(difluoromethoxy)-1,1,1,2-tetrafluoroethane, is described wherein the highly purified opposite optical isomer of iso-flurane is reacted with bromine trifluoride in the cold, preferably in the presence of a solvent. A preferred solvent is bromine. The highly purified positive isomer of desflurane is advantageous over the negative isomer or the racemate.

3 Claims, No Drawings

PREPARATION OF PURIFIED OPTICAL ISOMERS OF DESFLURANE

This is a division, of application Ser. No. 07/959,204, filed Oct. 9, 1992, which is a continuation of application Ser. No. 07/802,115 filed Dec. 4, 1991, both now abandoned.

This invention relates to inhalation anesthetics, more particularly to the highly purified optical isomers of desflurane and a process for their preparation.

BACKGROUND OF THE INVENTION

Desflurane, 2-(difluoromethoxy)-1,1,1,2-tetrafluoroethane, is an inhalation anesthetic possessing very advantageous properties. Desflurane is of significant commercial potential, in particular, as a result of being an effective anesthetic which demonstrates rapid induction and an unexpectedly rapid recovery from anesthesia. The latter property makes it especially attractive for surgical procedures done on an out-patient basis.

Desflurane is disclosed in Example XXI of Russell et al, U.S. Pat. No. 3,897,502, issued Jul. 29, 1975, which is directed to processes for making fluorinated ethers which are useful as solvents to prepare pastes and dispersions of fluorine-containing olefins and fluorowaxes, and as degreasing agents. The use of desflurane as an anesthetic is patented in Terrell, U.S. Pat. No. 4,762,856, issued Aug. 9, 1988.

The development of desflurane, typical of the highly fluorinated, volatile anesthetic ethers known in the art, has been as a racemic mixture since, heretofore, separation into the component enantiomers has not proven feasible and all known syntheses produce the racemic mixture. In fact, there is only a single fluorinated anesthetic for which the separation into optical isomers has been reported in the literature, F. Y. Edamura et al, 159th American Chemical Society National Meeting Orgn. Abstract No. 84, (1970). However, this anesthetic, halothane ($CF_3CHClBr$), is not a fluorinated ether. Although the separation of enantiomers of halothane is reported by J. J. Kendig, et al, Anesthesiology, Vol. 39, (1973), p 518, there is no indication given of the optical purity thereof, nor is there any indication that either isomer was ever tested in vivo for pharmacologic activity. Finally, there is no suggestion given that the reported technique would have applicability to fluorinated ether structures.

In accordance with the present invention, a process has been found to synthesize and isolate the optical isomers of desflurane in high optical purity, i.e. in excess of 90 percent optically pure. It has been found that the optical isomers of desflurane, prepared and isolated in high purity, differ significantly in pharmacologic response and that the highly purified positive isomer is unexpectedly advantageous as an inhalation anesthetic.

SUMMARY OF THE INVENTION

A process is described for the preparation in high purity of the (+) and (−) isomers of 2-(difluoromethoxy)-1,1,1,2-tetrafluoroethane by the reaction of an enantiomer of isoflurane and bromine trifluoride.

DETAILED DESCRIPTION OF THE INVENTION

In accordance with the present invention, highly purified enantiomers of 2-(difluoromethoxy)-1,1,1,2-tetrafluoroethane, hereafter desflurane, are prepared by the reaction of bromine trifluoride with highly purified enantiomers of isoflurane, i.e. 2-(difluoromethoxy)-1,1,1-trifluoro-2-chloroethane.

Isoflurane has been for a number of years the most widely used inhalation anesthetic in the United States. As is the case with other halogenated ether inhalation anesthetics, it has been utilized as the racemate. The highly purified (+) and (−) isomers of isoflurane can be prepared in accordance with the method of our U.S. patent application Ser. No. 07/550,417, filed Jul. 10, 1990, which comprises: reacting 2,2,2-trifluoroethanol with a halodifluoroacetic acid or its corresponding alkyl ester in alkaline medium according to the reaction

$$CF_3CH_2OH + XCF_2CO_2R \rightarrow CF_3CH_2OCF_2COOH$$

wherein X is halogen other than fluoro and R is hydrogen or a lower alkyl group.

The reaction mixture is acidified, and the resulting acid converted to the acyl halide by reaction with, e.g. benzoyl chloride, phthaloyl chloride and thionyl chloride. The acyl halide is then reacted with chlorine gas according to the reaction

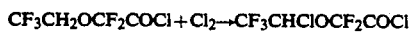

$$CF_3CH_2OCF_2COCl + Cl_2 \rightarrow CF_3CHClOCF_2COCl$$

the product is purified and hydrolyzed under reflux to form racemic 1-chloro-2,2,2-trifluoroethoxy difluoroacetic acid according to the reaction

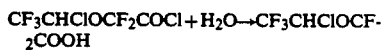

$$CF_3CHClOCF_2COCl + H_2O \rightarrow CF_3CHClOCF_2COOH$$

Resolution of racemic 1-chloro-2,2,2-trifluoroethoxy difluoroacetic acid into its enantiomers is carried out by reaction with a known resolving agent, e.g. R-(+)-dehydroabietylamine, to yield a solid salt which is separated from the mother liquor and recrystallized in a suitable medium such as ethyl acetate or acetonitrile. This diastereomeric salt is assigned (−)(+) on the basis of demonstrating a negative specific optical rotation in methanol. The positive diastereomer (+)(+) is obtained from the mother liquor by recrystallization utilizing a suitable organic medium such as chloroform, toluene, benzene, carbon tetrachloride, methylene chloride, tetrahydrofuran, dioxane and the like.

The dehydroabietylamine salts of the individual isomers can be converted to optically active isoflurane by heating with a mixture of water, a not greater than an equimolar quantity of a suitable base, preferably an inorganic base, such as potassium or sodium hydroxide, and a water-miscible, high boiling organic solvent, such as ethylene glycol or diethylene glycol, to a temperature of from about 160°–255° C. Preferably, the salts are heated in a mixture of water, diethylene glycol and potassium hydroxide.

In accordance with the present invention, highly purified optical isomers of desflurane are prepared by reaction of the purified optical isomer of isoflurane with bromine trifluoride at low temperature, preferably in the presence of a solvent.

It is taught in Robin et al, U.S. Pat. No. 5,015,781, that desflurane can be prepared by the reaction of isoflurane and bromine trifluoride. It is considered unexpected, however, that bromine trifluoride reacts with the highly purified optical isomers of isoflurane to form the highly purified optical isomers of desflurane in view of the fact that antimony pentachloride/HF, which is also known to react with isoflurane to form desflurane, produces a racemic mixture of desflurane upon reaction with either highly purified optical isomer of isoflurane. Further, antimony pentachloride/HF also partially racemizes the unreacted isoflurane isomer.

Unpredictably, the bromide trifluoride reaction causes an almost complete inversion of sign with a small degree of retention or racemization. It has been found that reaction of the isoflurane isomers in high optical purity, i.e. 99–100% ee, with bromine trifluoride will yield the opposite sign optical isomer in about 91% optical purity, i.e. 91% ee. The reaction is run at temperatures below 0° C., preferably from about −20° C. to −10° C. Since unreacted bromine trifluoride readily solidifies at such temperatures, it is preferred to conduct the reaction in the presence of a solvent.

The choice of a solvent is difficult because of side reactions and/or poor solubility of bromine trifluoride. 1,1,2-Trichloro-1,2,2-trifluoroethane, for example, causes partial racemization in the reaction thereby markedly reducing the optical purity. Perfluorooctanes and perfluoro-2-butyltetrahydrofuran have the disadvantage of being poor solvents for bromine trifluoride, thus not permitting the reaction to be conducted at temperatures below 0° C. The preferred solvent for the subject reaction is liquid bromine. Liquid bromine is particularly advantageous in that it also serves as a reaction promoter.

In accordance with the present invention, an optical isomer of isoflurane in high optical purity, i.e. at least about 95% ee, preferably 99% ee or above, is combined with, on a mole-for-mole basis, from 0 to about 1.85, preferably from about 0.05 to 0.10 mole of liquid bromine and the mixture cooled to below 0° C., preferably from 0° to about −20° C., most preferably from about −10° to −20° C. Bromine trifluoride is then slowly added to the mixture until an excess has been added. Typically, based on the moles of isoflurane isomer present, from about 0.8 to 1.9, preferably from about 0.8 to 1.1, moles of bromine trifluoride are added to the mixture. Because bromine trifluoride solidifies at about 8° C., it is added to an isoflurane/liquid bromine mixture in the proportions stated above, which will not freeze at −20° C. Therefore, adding bromine trifluoride to isoflurane/liquid bromine is preferred because it offers better control of the reaction temperature. Good temperature control is crucial to obtaining a product with high optical purity.

After addition of the bromine trifluoride is completed, the reaction mixture is allowed to slowly warm to ambient and then heated to a temperature of about 50° to 70° C., preferably from about 55° to 62° C., to distill off all of the low-boiling products. Desflurane is collected in appropriate cold traps and purified. The yield, typically, is from about 70 to 78%.

It has been found that the highly purified positive isomer of desflurane is unexpectedly advantageous in comparison to the negative isomer or the racemate in that it has a greater potency. Further, the positive isomer has been demonstrated to be superior to the racemate and the negative isomer in terms of the time in which a patient would become "street fit". "Street fit" is used to connote that a patient has regained full equilibrium, balance, and the like so that he or she can leave the hospital or physician's office. This is a significant advantage when one considers the increasing number of surgical procedures which are conducted on an outpatient basis.

The highly purified positive isomer of desflurane is administered to an anesthetic susceptible mammal in a respirable mixture containing a life-supporting concentration of oxygen. In general, such mixtures will contain from a fraction, e.g. about 4 percent by volume, up to about 10 percent by volume of highly purified (+) desflurane in oxygen. As is well known by those skilled in the art, the effective amount of highly purified (+) desflurane in such mixtures will depend on conventional criteria, such as the depth of anesthesia to which the mammal is to be brought, the rate at which anesthesia is to be induced, and the length of time over which anesthesia is to be maintained. As is the case with racemic desflurane and commercial anesthetics of its class, such as isoflurane, it is preferred to administer the highly purified positive isomer of desflurane in a mixture of nitrous oxide and oxygen. Such mixtures will contain from about 2 to about 5 percent by volume of the isomer with the remainder typically comprising a 70/30 by volume mixture of nitrous oxide and oxygen.

The following Examples further illustrate this invention, it being understood that the invention is in no way intended to be limited to the details described therein. In the Examples, all parts and percentages are on a weight basis and all temperatures are in degrees Celsius, unless otherwise stated.

EXAMPLE 1

Preparation of
(+)-2-(difluoromethoxy-1,1,1,2-tetrafluoroethane
(desflurane).

Bromine trifluoride, 6.8 mL (0.14 mol, d=2.8 g/mL), was added, dropwise, from a graduated glass addition funnel, to a mixture (precooled to −18°) of 25.0 g (0.14 mol) of 98.5% ee (−)-isoflurane and 0.5 mL (9.7 mmol, d=3.1 g/mL) of bromine in a glass reaction flask under $N_2$ equipped with a stirring bar, a thermometer and a dry ice condenser connected to an ice water trap and then a dry ice trap. The reaction occurred within fifteen minutes as indicated by a mild exotherm and solid bromine sublimination. When 1.5 mL of bromine trifluoride has been added, a mild reflux was observed and more bromine solid formed on the dry ice condenser. Near the end of the reaction, the mixture became a slurry. The addition consumed 6.1 hours at −18° to −13°. The reaction mixture was stirred at −18° to −10° for two hours and then maintained at −14° for an additional twelve hours. The mixture was warmed slowly to ca. 20° in a water bath and, thereafter, heated to 62° to expel all low boiling products. The liquids containing bromine which collected in the traps were washed three times with ice-cold 10% aqueous NaOH to destroy residual bromine. The organic liquids were combined and washed three times with ice water. The aqueous layer of the last wash was approximately neutral to pH paper. The wet organic liquid was dried at −78° and removed. The remaining ice was melted, the trapped organic liquid washed again with water, and dried at −78° to collect more product. This procedure was repeated a third time. The dry organic liquids were combined to give 17.2 g of crude product. Distillation, from bulb to bulb, under vacuum, afforded 16.1 g (70.6%) of (+)-desflurane at a chemical purity of 99.7% (GC) and a optical purity of 91.7% ee (chiral GC).

Optical rotation: $[\alpha]_D^{25} = +29.0°$, $[\alpha]_{365}^{25} = +84.4°$, neat.

$^1$H NMR (CDCl$_3$): δ 5.9 (d of q, J$_{FCH}$=54.4 Hz, J$_{FCCH}$=2.9 Hz, CFH), δ 6.5 (t, J$_{FCH}$=70.4 Hz, CF$_2$H).

$^{19}$F NMR (CDCl$_3$, proton decoupled): δ −84.4 (s, CF$_3$), δ −85.1 and −86.7 (two d, J$_{FCF}$=160.8 Hz. nonequivalent CF$_2$), δ −146.5 (s, CHF).

EXAMPLE 2

Preparation of (−)-2-(difluoromethoxy)-1,1,1,2-tetrafluoroethane.

Following the procedure of Example 1, 4.4 mL (0.09 mol) of bromine trifluoride was added to a mixture of 20.0 g (0.11 mol) of 100% ee of (+)-isoflurane and 0.6 mL (11.6 mmol) of bromine at −20° to −15° over four hours under N$_2$. After work-up, 14.2 g (78.1%) of (−)-desflurane at a chemical purity of 99.8% (GC) and an optical purity of 91.1% ee (chiral GC) was obtained.

Optical rotation: [α]$_D^{25}$=−29.2°, [α]$_{365}^{25}$=−85.2°, neat.

$^1$H NMR and $^{19}$F NMR spectra (CDCl$_3$) were the same as those from (+)-desflurane.

EXAMPLE 3

Reaction of (−)isoflurane and HF/SbCl$_5$.

To a mixture of 3.6 g (0.18 mol) of anhydrous HF and 0.6 g (2.0 mmol) of antimony pentachloride under N$_2$ in a 30 mL reactor fitted with a thermometer and two dry ice traps in series, was added over fifteen minutes at −12° to −10° 3.0 g (16.2 mmol, 99.0% ee) of (−)-isoflurane. All equipment was coated with polytetrafluoroethylene. A mild exothermic reaction was observed. The mixture was stirred at −10° for 1 hour and then warmed to 12°. An equal volume of 10% aqueous NaOH solution was added slowly to the reaction mixture. An organic liquid, 1.8 g, was isolated. GC analysis of this liquid showed that it was a mixture of 15% desflurane and 85% isoflurane. The conversion was 9.5% and the yield was 18.9%. Chiral GC analysis indicated that the desflurane was racemic and the (−)-isoflurane was partially racemized to 67.0% ee.

EXAMPLE 4

Reaction of (−)-isoflurane and BrF$_3$ in 1,1,2-trichloro-1,2,2-trifluoroethane.

(−)-Isoflurane, 3.0 g (16.2 mmol, 99.0% ee), was added gradually to a solution of 1.5 mL (30.7 mmol) of bromine trifluoride dissolved in 25 mL of CFCl$_2$CF$_2$Cl at 0° under N$_2$. The mixture was stirred at 0° for two hours. A red color indicating the presence of bromine gradually displaced the yellow color which was indicative of bromine trifluoride. The reaction mixture was slowly warmed to ambient temperature over two hours, and then heated to 42°. The liquid collected in dry ice traps was dried at −78° to give 2.1 g of a product which was shown by GC analysis to contain 39.3% of desflurane and 60.1% of a mixture of CFCl$_2$CF$_2$Cl and isoflurane. Chiral GC analysis of the (−)-desflurane showed 59.2% ee. Conversion to desflurane was 29.7%.

EXAMPLE 5

Preparation of the Optical Isomers of Desflurane without the Addition of Bromine.

Utilizing the apparatus described in Example 1, bromine trifluoride, 1.1 mL (22.5 mmol), was added dropwise at ambient temperature to (+)-isoflurane, 10.6 g (57.5 mmol, 97% ee). over thirty minutes. The product was collected and purified as in Example 1. There was obtained 2.2 g of a first product which was shown by GC analysis to be 34.7% (−)-desflurane and 64.6% (+)-isoflurane. The optical purity of (−)-desflurane, by chiral GC analysis was 80.0% ee. A second liquid fraction, isolated from the dry ice trap, contained 38.0% of (−)-desflurane (78.4% ee) and 59% (+)-isoflurane.

The procedure was repeated using (−)-isoflurane, 5.0 g (27.1 mmol, 99.0% ee), which was added dropwise to 1.4 mL of bromine trifluoride (28.6 mmol) at 0°. The reaction did not start for about twenty minutes, and the addition of isoflurane required one hour. The mixture was stirred for an additional hour, after which it was allowed to warm to ambient temperature. The product was collected and purified to yield 1.7 g of liquid which was 97% (+)-desflurane and 2.7% (−)-isoflurane. The optical purity of (+)-desflurane was 86.1% ee by chiral GC analysis.

EXAMPLE 6

Preparation of (+)-desflurane using a ratio of 0.27 mole of bromine per mole of (−) isoflurane.

Utilizing the procedure and apparatus of Example 1, 20.0 g (0.11 mol, 98.5% ee) of (−)-isoflurane and 1.5 mL (29.0 mmol) of bromine were combined and cooled to −15°. There was some solidification of bromine. Bromine trifluoride (4.7 mL, 96.1 mmol), was added dropwise over three hours maintaining the temperature between −15° and −19°. About ten minutes after initiation of the addition of bromine trifluoride, there was a mild exotherm with the sublimation of bromine. The mixture was stirred at −15° for an additional two hours, allowed to warm to room temperature, after which the product was recovered and purified in accordance with the procedure of Example 1. There was obtained 12.8 g (70.3% yield) of (+)-desflurane which was 99.5% chemically pure and 90.5% ee optically pure.

EXAMPLE 7

Male Swiss-Webster mice, about 22–25 g, were allowed free access to food and water and housed ten to a cage in a temperature (22.2°) and humidity (50%) controlled vivarium with a twelve hour light-dark cycle.

The test anesthetic was pipetted into a 1900 ml container previously flushed for one minute with 100% oxygen. The container was sealed, rotated to insure complete evaporation of test compound and allowed to stand for five minutes. The approximate concentration of the anesthetic was calculated. Six animals were tested at each concentration of racemate and its purified optical isomers. The animals were placed in the container in groups of three. The container was rotated periodically.

The percentage of mice to lose their righting ability within two minutes and remain supine for thirty seconds was noted. Loss of righting (LOR) at four concentrations, including EC$_0$ and EC$_{100}$, were used to determine the EC$_{50}$. Subsequently, onset (defined as the mean time for six animals to LOR) and recovery (defined as the mean time to ambulation) were determined at the EC$_{50}$ concentration. Potency (defined by the dose-response curve) of each compound was compared using a parallel line analysis. Onset and recovery means were compared using a Student's T-Test P<0.05. The results are reported in Table I. In the Table, "S.D." is standard deviation, "C.L." is confidence level and "EC$_{50}$" is the effective concentration in one half of the animals tested.

TABLE I

| | In the Mouse | |
|---|---|---|
| Racemic Desflurane | Positive Isomer | Negative Isomer |
| $EC_{50} = 4.75\%$ | $EC_{50} = 4.1\%$* | $EC_{50} = 4.6\%$ |
| C.L. = 4.4–5.1 | C.L. = 3.8–4.4 | C.L. = 4.3–4.9 |
| Onset = 1.72 min | Onset = 1.44 min | Onset = 1.05 min |
| S.D. = 0.35 | S.D. = 0.25 | S.D. = 0.17 |
| Recovery = 0.12 min | Recovery = 0.31 min | Recovery = 0.25 min |
| S.D. = 0.08 | S.D. = 0.25 | S.D. = 0.10 |

*Significant at $P<0.05$.

This test demonstrates improved potency of the highly purified positive isomer of desflurane.

EXAMPLE 8

Male Sprague-Dawley rats were maintained as were the mice in Example 7. The animals were trained to maintain their balance for ninety seconds on a rotarod revolving at 10 rpm. The animals were allowed to rest five minutes and again trained to remain on the rotating rotarod for ninety seconds.

The rats were individually placed into containers which had been purged with 100% oxygen for one minute, and which contained a known concentration of racemic desflurane, or its positive isomer or negative isomer which had been previously determined to be equal to the $EC_{100}$. Five rats were utilized for each anesthetic.

The onset of LOR was recorded for each animal. The animals remained in the container for five minutes following LOR, and were then removed. Recovery was determined, and the mean calculated.

Following recovery of righting, the animals were placed on the rotarod 0, 90, and 180 seconds thereafter and the length of time they were able to remain on the rod was recorded in each instance. Animals that remained on the rod for a full ninety seconds were not subsequently tested. The durations of maintaining balance were noted and averaged, and the number of animals meeting the ninety second criterion were recorded at each time interval.

A Rotarod Index (ROI) was then calculated according to the following formula.

$ROI = (First + Second \times \frac{2}{3} + Third \times \frac{1}{3})/3$ where First, Second and Third are the average time on the rod in seconds for the respective time intervals. Animals remaining on the rod for the full ninety seconds during either the interval beginning at zero time or ninety seconds were scored with ninety seconds for all subsequent intervals. Therefore, the maximum ROI attainable was $(90 + 90 \times \frac{2}{3} + 90 \times \frac{1}{3})/3 = 60$. The ROI value measures the recovery of motor coordination following drug-induced LOR.

Onset and recovery were compared across anesthetics using a Student's T Test. The results are given in Table II.

TABLE II

| | Rotarod Testing In Rats (Time in Minutes) | |
|---|---|---|
| Racemic Desflurane | Positive Isomer | Negative Isomer |
| Onset = 1.04 | Onset = 0.92 | Onset = 1.05 |
| S.D. = 0.26 | S.D. = 0.20 | S.D. = 0.26 |
| Recovery = 1.38 | Recovery = 0.88 | Recovery = 0.31 |
| S.D. = 0.61 | S.D. = 0.70 | S.D. = 0.15 |
| ROI = 32.4 | ROI = 38.6 | ROI = 28.8 |

The results indicate that, although the negative isomer demonstrated a faster recovery time, the positive isomer was clearly superior in the rotarod test because of the larger ROI value which is an indication that a patient would more rapidly become "street fit" in terms of, e.g. equilibrium.

We claim:

1. A method of producing a highly purified optical isomer of 2-(difluoromethoxy-1,1,1,2-tetrafluoroethane comprising reacting the opposite optical isomer of isoflurane in at least 95% optical purity with bromine trifluoride at a temperature between about 0° and −20° in the presence of bromine as a solvent.

2. A method in accordance with claim 1, wherein the optical isomer of isoflurane is at least 99% optically pure.

3. A method in accordance with claim 1, wherein the reaction is carried out at a temperature of from about −10° to about −20°.

* * * * *